United States Patent [19]

Bement et al.

[11] Patent Number: 5,052,817
[45] Date of Patent: Oct. 1, 1991

[54] IGNITABILITY TEST METHOD AND APPARATUS

[75] Inventors: Laurence J. Bement, Newport News; James W. Bailey, Tabb, both of Va.; Morry L. Schimmel, St. Louis, Mo.

[73] Assignee: The United States of America as represented by the Administrator of the National Aeronautics and Space Administration, Washington, D.C.

[21] Appl. No.: 593,412

[22] Filed: Oct. 4, 1990

Related U.S. Application Data

[63] Continuation-in-part of Ser. No. 426,345, Nov. 30, 1989, abandoned.

[51] Int. Cl.$^5$ ............................................. G01N 25/50
[52] U.S. Cl. ......................................... 374/8; 73/167; 102/200
[58] Field of Search ............. 374/8; 73/167; 102/204, 102/470, 202.5, 200

[56] References Cited

U.S. PATENT DOCUMENTS

| H441 | 3/1988 | Milton et al. | 374/8 |
| 4,033,897 | 7/1977 | Barnard, Jr. | 374/8 |
| 4,759,215 | 7/1988 | Atchley et al. | 374/51 X |

Primary Examiner—Daniel M. Yasich
Attorney, Agent, or Firm—George F. Helfrich

[57] ABSTRACT

An apparatus for testing ignitability of an initiator includes a body having a central cavity, initiator holder for holding the initiator over the central cavity of the body, an ignition material holder disposed in the central cavity of the body and having a cavity facing the initiator holder which receives a measured quantity of ignition material to be ignited by the initiator and a chamber in communication with the cavity of the ignition material and the central cavity of the body, and a measuring system for analyzing pressure characteristics generated by ignition of the ignition material by the initiator. The measuring system includes at least one transducer coupled to an oscillograph for recording pressure traces generated by ignition.

9 Claims, 4 Drawing Sheets

IGNITABILITY TEST METHOD AND APPARATUS

ORIGIN OF THE INVENTION

The invention described herein was made in the performance of work under a NASA contract and is subject to the provisions of Section 305 of the National Aeronautics and Space Act of 1958, as amended, Public Law 85-568 (72 Stat. 435; 42 USC 2457).

CROSS-REFERENCE

This application is a continuation-in-part of co-pending application Ser. No. 07/426,345, filed Nov. 30, 1989 now abandoned.

BACKGROUND OF THE INVENTION

1. Field of the Invention

The present invention relates generally to the field of measuring and testing, and more specifically, to a test apparatus and method for determining the ignition performance of ignition devices, i.e., devices that produce flame.

2. Description of the Related Art

Ignition of propellant materials used in rocket motors, or munitions, or even automobile air bags, all start with an igniter or initiator which can be fired either electrically or mechanically. Percussion primers are one type of munitions application. Percussion primers are generally about 0.2 inch or less in diameter and consist of thin wall brass cups containing friction-sensitive pyrotechnic compositions and an internal anvil. Impacting and deflecting the bottom of one of the cups compresses the pyrotechnic composition against the anvil to achieve ignition, thereby outputting a quantity of heat, light, gas and burning particles.

Percussion primers have been in use for over one hundred years. Over this time, test methods and apparatuses have been devised to measure different aspects of an ignition output, such as heat, light, pressure, and burning particles. Heat output has been measured with calorimeters and light output has been measured with photocells and photographs of an ignition output's light and burning particles in a darkened room and with the aid of vented test volumes. Pressure measurements have been made by simply having an operator listen to relative sound of the output in vented test fixtures, and by measuring the pressure in closed test volumes.

Tests of the effect of burning particles are made in a vented volume and by a "standoff" method. In the latter, a primer is fired into a large, deep volume with a test propellant at the base. The depth is varied until ignition fails to occur.

One of the disadvantages common to the above-mentioned test methods and apparatuses is that virtually all system-level tests have been performed on a go/no-go basis. That is, a system or sub-system is assembled and then initiated. The results will show that the tested initiator, such as a percussion primer, either did or did not work properly. Thus, the tests do not provide sufficient information on actual ignition interfaces used in ignition system designs. Consequently, little technical understanding has been achieved in determining the relative importance of system variables and functional margins. Individual measurements of heat, light, pressure, and burning particles cannot be adequately extrapolated to a system-level performance. For example, the large volumes in all of the above-mentioned test apparatuses are not representative of actual applications. The volumes reduce the available pressure and allow heat to dissipate, even to the point of quenching the burning particles.

Generally, the known methods and apparatuses discussed above only provide relative comparisons, which often depend on operator judgment. These tests are incapable of measuring ignition within the first millisecond.

Ignitability has particular significance to aerospace applications where there is a need to measure how well an initiating element can ignite other materials. Specifications require that igniters fire when supplied with sufficient electrical or mechanical input energy. For some devices, such as the NASA standard initiator, (NSI), output is controlled by specifying pressure performance limits when fired into a closed volume (known as a "bomb") with no requirement for ignition by its output. However, no military specification or other generally accepted tests exist for measuring primer output, which is used only for ignition.

One specific test method and apparatus was developed for measuring energy output for many different kinds of explosive devices, including percussion primers. The apparatus included a piston/cylinder energy sensor containing a strength-calibrated, crushable honeycomb element. The output of a percussion primer was measured as the work done in stroking the piston to crush the honeycomb. Output was equated to the distance crushed multiplied by the crush strength of the honeycomb, and was expressed in units of inch-pounds.

Significantly, the most important percussion primer output parameter is not energy output to stroke a piston, but is instead the ignitability performance. A need exists to develop a test method and apparatus which will determine whether the primer will ignite the next item in the train, and with what margin.

SUMMARY OF THE INVENTION

An object of the present invention is to provide a test method and apparatus capable of providing quantitative measurements of the efficiency of all types of initiators, one type thereof being percussion primers.

Another object of the invention is to provide a relatively simple method of comparing output performance of percussion primers and other initiators in terms of ability to ignition typical ignition and propellant materials.

A further object of the invention is to provide a test method and apparatus that determines the output delay and function time of initiators such as percussion primers.

In a preferred embodiment, an apparatus for testing ignitability of an initiator includes a body having a central cavity, an initiator holder for holding the initiator over the central cavity of the body, an ignition material holder disposed in the central cavity of the body and having a cavity facing the initiator holder which receives a measured quantity of ignition material to be ignited by the initiator and a chamber in communication with the cavity of the ignition material holder and the central cavity of the body, and means in communication with the central cavity of the body for measuring, recording and analyzing pressure characteristics generated by ignition of the ignition material by the initiator. Firing the initiator into the ignition material causes the ignition material to ignite, and the pressure generated in the closed chamber is measured as a function of time to generate a pressure trace. Preferably, the method includes measuring pressure at one millisecond, time to reach 50 percent peak pressure, and time to reach peak pressure and determining initiator output delay and function time to achieve initiation. "Ignitability" is then expressed as the ratio of one millisecond pressure to peak pressure. This ratio can be compared to ratios similarly devised using other materials to provide comparative results.

These objects, together with other objects and advantages which will be subsequently apparent reside in the details of construction and operation of the apparatus and method steps as more fully hereinafter described and claimed, reference being had to the accompanying drawings forming a part hereof, wherein like reference numerals refer to like parts throughout.

DETAILED DESCRIPTION OF THE PREFERRED EMBODIMENTS

The aforementioned drawings will be discussed with reference to examples of test materials, such as percussion primers and ignition materials. In conducting tests using the apparatus and method of the present invention, the following percussion primers were used:

| Ingredients | Percentage by Weight |
|---|---|
| Percussion Primer I | |
| Diameter - 0.1748 to 0.1756 inch; Height - 0.111 to 0.119 inch | |
| Composition | |
| Lead Styphnate | 53 |
| Barium Nitrate | 22 |
| Antimony Sulfate | 10 |
| Aluminum (powdered) | 10 |
| Tetracene | 5 |
| Percussion Primer II | |
| Diameter - 0.1748 to 0.1756 inch; Height - 0.111 to 0.119 inch | |

-continued

| Ingredients | Percentage by Weight |
|---|---|
| Composition | |
| Lead Thiocyanate | 25 |
| Potassium Chlorate | 33 |
| Antimony Trisulfide | 25 |
| TNT | 3 |
| Calcium Silicide | 14 |

The two primers I and II, are available as percussion primers M42C1-PA101 and M42C2-793, respectively, and were selected for their markedly different output performances. The output of Primer I is considerably more brisant than Primer II, due to Primer I's lead styphnate content.

Ignition materials used for testing are identified as follows:

| Nomenclature | Material | Physical Description |
|---|---|---|
| FFFG | Black Powder | 0.020 to 0.030 in. granules |
| FFG | Black Powder | 0.020 to 0.060 in. granules |
| A-Cannon | Black Powder | 0.125 to 0.250 in. platelets (0.60 in thickness) |
| 20/40 | Boron-Potassium Nitrate (BKNO$_3$) | Salt to flour consistency |
| Type I (6/12) | (BKNO$_3$) | 0.60 to 0.130 granules |
| Type 2R Pellets | (BKNO$_3$) | 0.125 DIA × 0.100 height, domed ends |

The ignition materials were selected to provide a wide range of initiation sensitivities and burning rates. That is, the finer powders and granules would be expected to ignite more easily and burn more rapidly than the larger granules and pellets. Black powder and boronpotassium nitrate are the most extensively used ignition materials.

Figure 1:
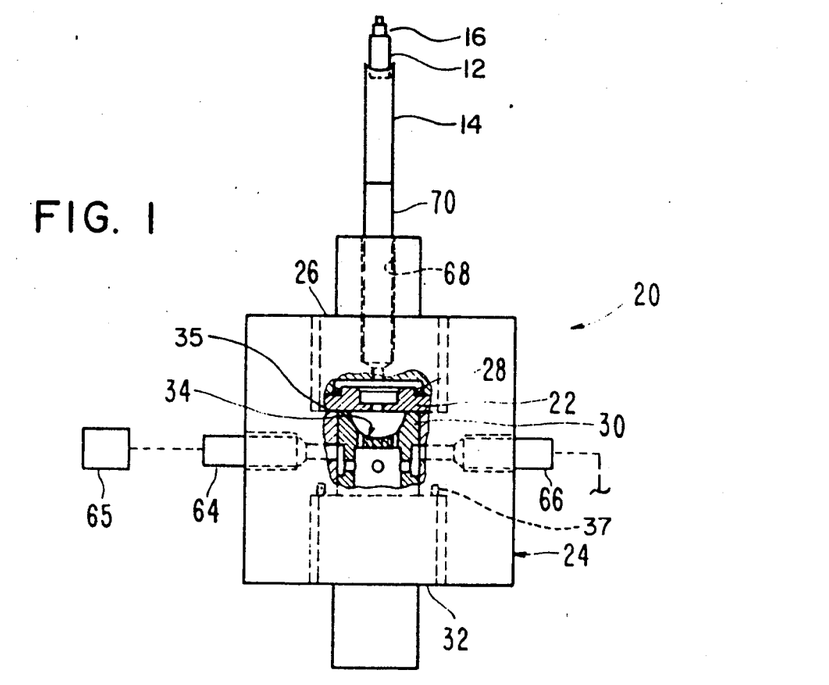
FIG. 1 is a cross-sectional view of an apparatus for testing ignitability of an initiator according to the present invention.

The test apparatus of the present invention is generally referred to in FIG. 1 by the numeral 20.

A percussion primer is pressed into a primer holder 22 which is placed into an upper cavity of a body 24. An adapter 26 threads down onto the primer holder 22 in order to firmly hold the primer holder in the upper cavity of the body 24 and over a central cavity. An O-ring 28 provides a pressure seal between the adapter 26 and the primer holder 22.

An ignition material holder 30 is disposed in a central cavity of the body between the primer holder 22 and a plug 32 threaded into a lower cavity provided in the body 24. The material holder 30 has a hemispherical cavity 34 facing the primer holder 22 which, when performing a test, is designed to receive a quantity of ignition material (in one embodiment about 200 mg). The ignition material is weighed out and inserted into the hemispherical cavity 34 prior to assembly of the apparatus. In the embodiment of the invention which uses about 200 mg of material, the hemispherical cavity 34 has a diameter of 0.435 inch.

Figure 2:
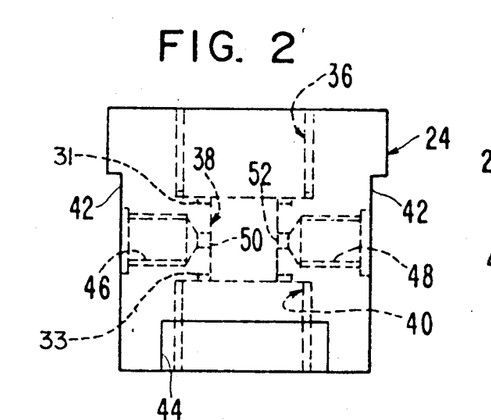
FIG. 2 is a cross-sectional view of a portion of the apparatus illustrated in FIG. 1.
Figure 3:
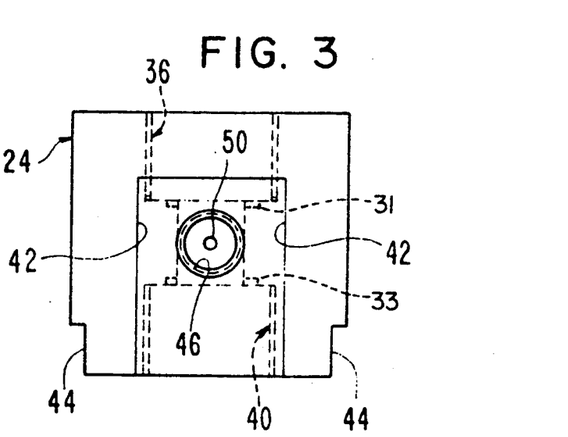
FIG. 3 is a view similar to FIG. 2, turned 90 degrees.
Figure 4:
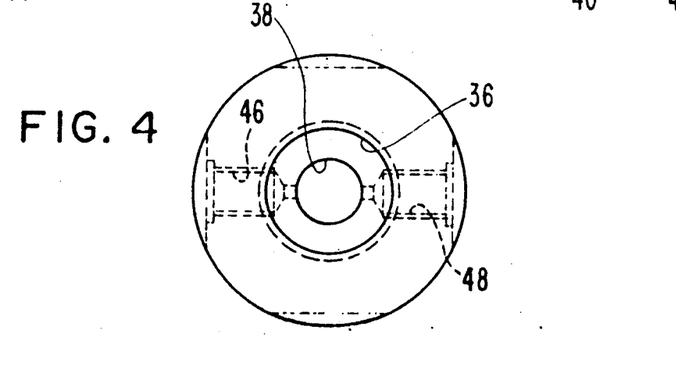
FIG. 4 is a top plan view of the portion illustrated in FIG. 2.

The body 24 is illustrated in FIGS. 2-4 prior to assembly with the other parts. These figures illustrate the upper cavity 36, the central cavity 38, and the lower cavity 40. The three cavities collectively form a longitudinal passageway through the body 24 which, upon assembly, receives the adapter 26, the material holder 30, and the plug 32, all of which are in end-to-end contact at opposite ends of the central cavity 38. Preferably, O-ring grooves 31 and 33 in body 24 allow placement of O-rings 35 and 37. The O-rings provide a combustion gas seal at the contacting ends of adapter 26, material holder 30, and plug 32.

The body 24 is substantially cylindrical in shape, except for parallel flattened surfaces 42 and 44. A pair of sockets 46 and 48 extend transversely through the body 24 from diametrically opposite sides of the central cavity 38. The sockets 46 and 48 have bores 50 and 52, respectively, which extend into communication with the central cavity 38.

Figure 5:
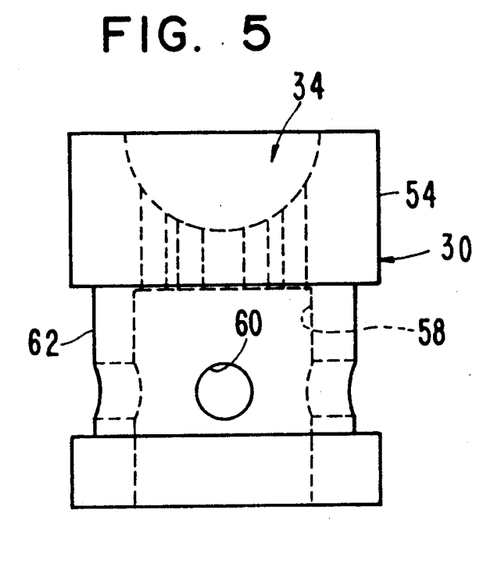
FIG. 5 is an enlarged, cross-sectional view of another portion of the apparatus of FIG. 1.
Figure 6:
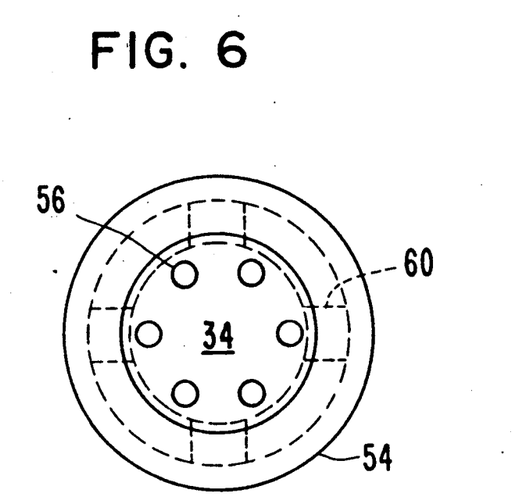
FIG. 6 is a top plan view of the portion illustrated in FIG. 5.

Referring to FIGS. 5 and 6, the material holder 30 is shown in greater detail by enlargement. The material holder 30 has an upper portion 54 in which the hemispherical cavity 34 is formed. Six axially oriented holes 56 extend from an outer region of the hemispherical surface of the hemispherical cavity to an axially disposed cylindrical chamber 58 formed in the material holder 30 below the upper portion 54. Four lateral holes 60, which are substantially horizontally coplanar, extend from the cylindrical chamber 58 to an annular recess 62 formed externally around the outer cylindrical surface of the material holder 30. Expanding hot gas and burning particles which pass through the six vertical holes 56 enter the cylindrical chamber 58 and exit therefrom through the lateral holes 60. When assembled into the body 24 of the test apparatus, the lateral holes 60 are disposed in a horizontal plane beneath the bores 50 and 52 so as to protect the transducers 64 and 66 (FIG. 1) which are fitted into the sockets 46 and 48, respectively. The annular recess 62 allows the hot gas and thus the pressure generated by ignition, to be communicated to the transducers.

When assembled, the hemispherical cavity 34 and the cylindrical chamber 58, which are in communication with each other by virtue of the vertical holes 56, are sealed at opposite ends by the primer holder 22 and the plug 32.

Figure 7:
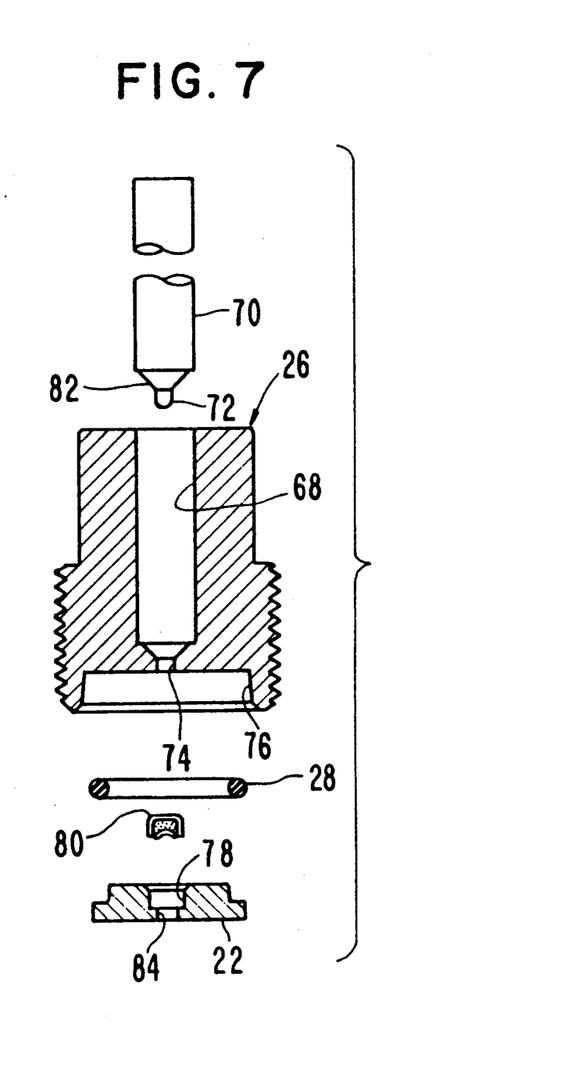
FIG. 7 is an exploded view of a sub-assembly of the apparatus of FIG. 1.

Referring to FIG. 7, the adapter 26 has a central bore 68 slidably receiving a firing pin mechanism 70 having a pin 72 at a proximal end thereof. Upon actuation of the firing pin mechanism, the pin 72 passes through an opening 74 to strike a primer held in the primer holder 22 which is received in a space 76.

Referring again to FIG. 1, a drop weight 12 provides actuation of the firing pin mechanism 70. A guiding means 14 such as a cylindrical tube guides the drop weight 12 to concentric impact on the firing pin mechanism 70. The drop weight 12 is set at a particular height to deliver a desired energy input. An accelerometer means 16 mounts on top of drop weight 12 as shown in FIG. 1 and records the time of impact of firing pin mechanism 70, thereby allowing determination of output delay and function time of the percussion primer.

The primer holder 22 has a cavity 78 which receives an initiator 80 such as a percussion primer. When the drop weight 12 thrusts the firing pin mechanism 70 downwardly to the full extent, the pin 72 strikes the upper portion of the percussion primer and thus fires the same. The percussion primer acts as a seal to prevent venting of pressure created during the burning of the ignition material.

In operation, the firing pin impacts the initiator 80 with about 100 inch-ounces of striking energy. Primer ruptures, caused by excessively deep penetration of the firing pin into the primer, are prevented by restricting the firing pin penetration to about 0.030 inch. The output of the percussion primer transfers through a spit hole 84 of the primer holder 22 onto the ignition material received in the hemispherical cavity 34. The high pressure gases, generated by the combustion of the ignition material vent through the six vertical holes 56 in the holder 30 into the cylindrical chamber 58 and subsequently to the pressure transducers 64 and 66. The transducer outputs are measured with an oscillograph 65 and recorded on magnetic tape and permanent records are created.

After testing, the apparatus is easily disassembled for cleaning to assure the same initial conditions exist for each firing.

The pressure transducers 64 and 66 are preferably piezoelectric type transducers, which are well known and commercially available. One such transducer is the KISTLER MODEL 601A. An associated measurement system measures pressure sensed by the transducers, and can include known components such as charge amplifiers, voltage amplifiers, a tape recorder and oscillograph, which has a frequency response that is preferably flat to 40 kHz.

The system will facilitate the creation of a "pressure trace" which is a graphical illustration of a pressure wave plotted on X and Y axes, with pressure on the Y-axis and time on the X-axis. These pressure traces are illustrated in FIGS. 8–11.

Tests performed with the ignition materials in the bottom of the central cavity 38 (thus resting on the upper surface of the plug 32 in the absence of the material holder 30) produced very little performance differences. To evaluate the ignition and burning rate extremes afforded by very fine to very coarse ignition materials, the 20/40 and 2R $BKNO_3$ materials were tested. Quantities were doubled to exaggerate potential differences of burning rate and peak pressures achieved. The pressure traces generated by either primer indicated poor ignition characteristics, that is, very slow (100 millisecond time frame) non-reproducible build-up of pressure. The material holder of the present invention was found to facilitate a better presentation of the ignition material to the output of the percussion primer, and provide a more controlled burning of the ignition material.

In using the ignition material holder 30 in the central cavity 38, the initiation and combustion characteristics improved immediately. Pressures rose quickly and the powdered ignition material was consumed in less than 10 milliseconds. The 20/40 $BKNO_3$ and FFFG black powder ignited very quickly, so that little differentiation could be made between the ignition performance of these two primers. Conversely, the 2R $BKNO_3$ pellets ignited so slowly that, again, differentiation could not be recognized between primers.

Figure 8:
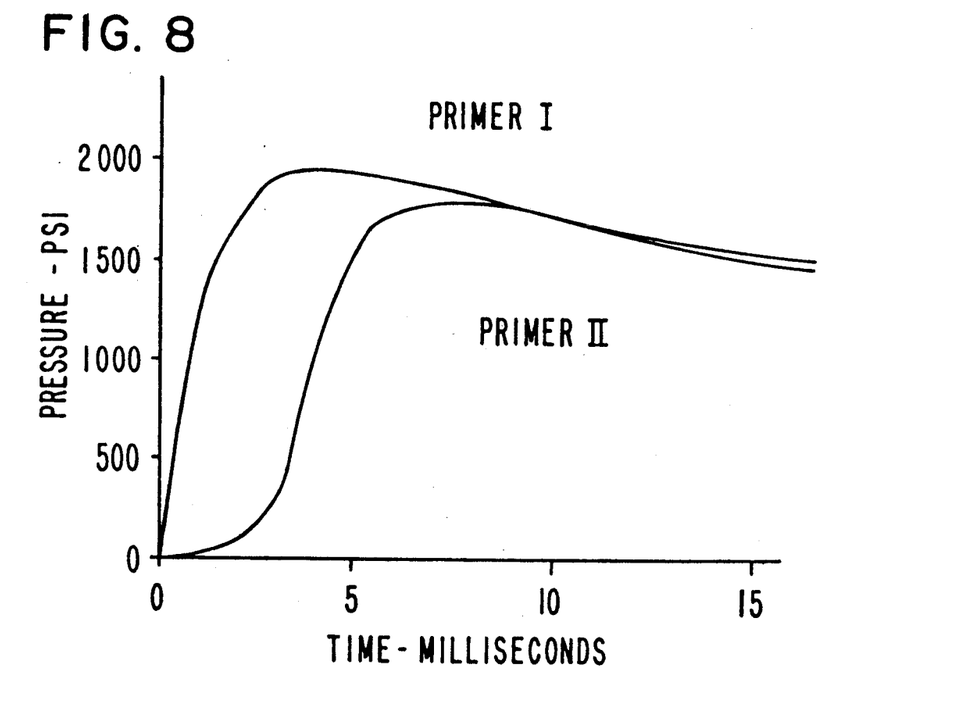
FIG. 8 is a graph illustrating a pressure trace of two different primer types (Primer I=M42C1 and Primer II=M42C2), both using the same type of ignition material (FFG black powder)

The first successful differentiation was achieved in using the FFG black powder, as shown in the graph of FIG. 8. The pressure produced by primer I rose immediately, and primer II produced an initial gradual increase, followed by a rapid rise in comparison to primer I.

Figure 9:
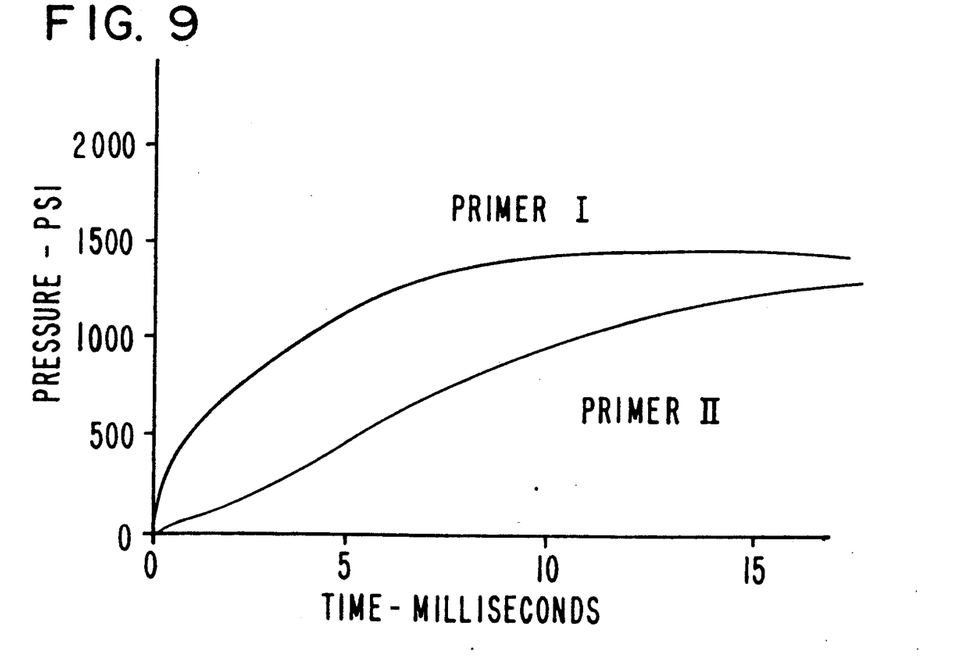
FIG. 9 is a graph showing a comparison of pressure traces produced by Primer I and Primer II percussion primers using A-Cannon black powder ignition material.

FIG. 9 shows the pressure traces produced when using the A-cannon ignition material. As before, the differences are significant.

Figure 10:
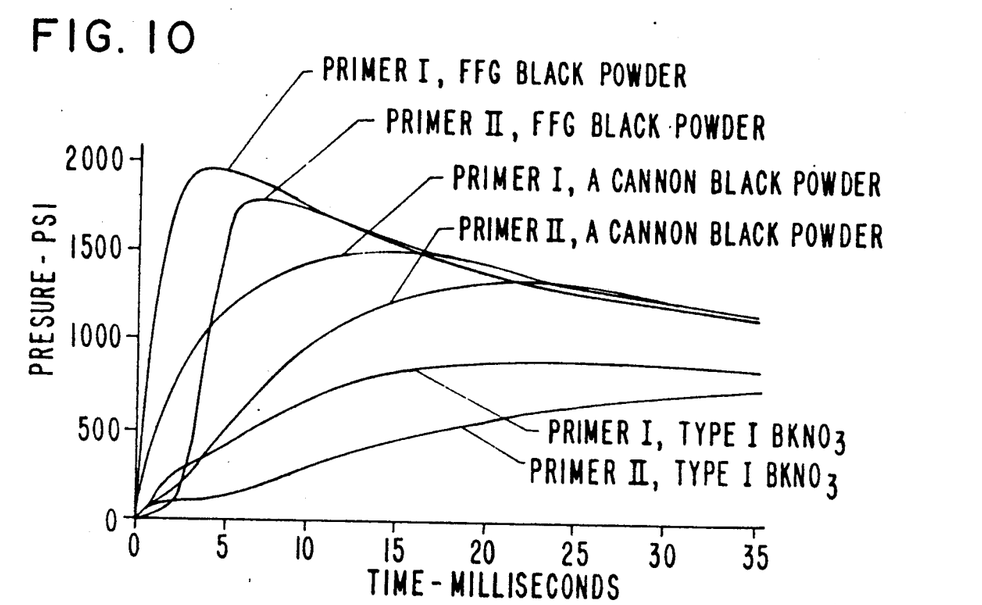
FIG. 10 is a graph showing typical pressure traces produced by the Type I and Type II percussion primers, using 200 mg each of three different ignition materials.

Two percussion primers, Primer I and Primer II were used in five tests, with each of the FFG and A-Cannon black powder and the Type I $BKNO_3$. Typical pressure traces generated by the parametric investigation were plotted on the same coordinate system and then analyzed to determine a statistical compilation and comparison of the performances achieved. A compilation of typical pressure traces produced by primer I and primer II percussion primers, using 200 mg each of the three different ignition materials is shown in FIG. 10 (which has a reduced time scale, compared to the preceding graphs).

Figure 11:
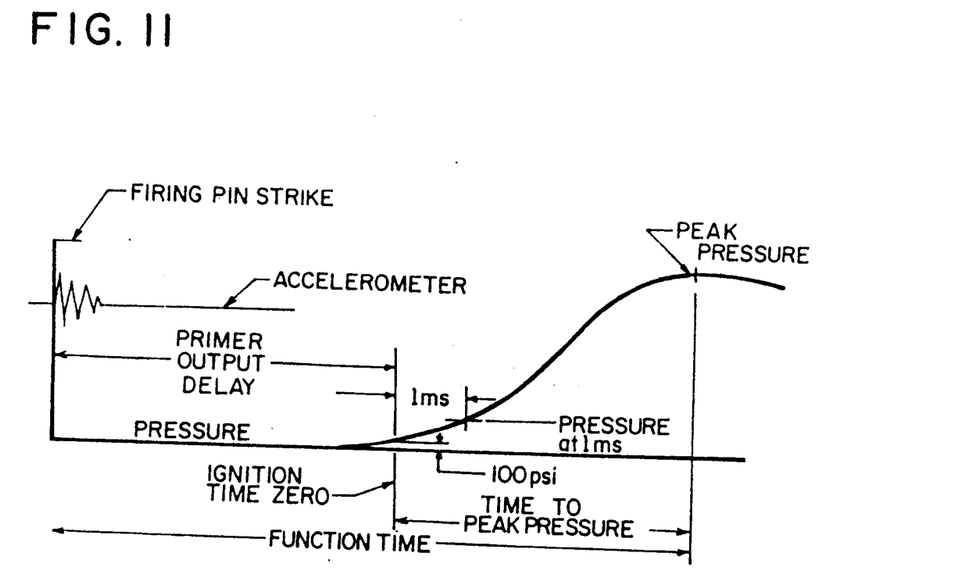
FIG. 11 is a graph illustrating a pressure trace, and data points selected for numerical description and analysis of ignitability according to the method of the present invention.

The data points selected to provide a numerical description and analysis of the pressure traces for the ignitability test method are shown in FIG. 11. Logical descriptives are the primer output delay, the function time, the time to reach 50% of peak pressure, and the peak pressure achieved. Another significant measurement is the pressure achieved at one millisecond.

The accelerometer 16 indicates the initiation input, occurring when drop weight 12 strikes firing pin mechanism 70. Primer output delay designates the time interval between the firing pin strike and the pressure trace reaching 100 psi. Selection of a pressure level of 100 psi avoids the difficulty of determining when the pressure rises above zero. Ignition time zero is then also at 100 psi. Since the major portion of both primers I and II heat contribution is achieved within the first millisecond, this time interval is significant for measuring primer initiation capability. According to the present invention, the ratio of the pressure at one millisecond to the peak pressure defines ignitability.

The following tables I–VI summarize test data obtained using the aforementioned descriptives. The initial comparison for each ignition material reveals that primer I achieved ignition sooner and more rapidly than did primer II. Secondly, the FFG black powder, using either primer (according to Tables I and II) produced the highest ignitability values (the ratio of pressure achieved at one millisecond over the peak pressure). The A-cannon black powder (Tables III and IV) was second, and the Type I BKNO$_3$, Tables V and VI, was third.

TABLE I

FUNCTIONAL DATA ON THE M42C1 PERCUSSION PRIMER USING 200 MG FFG BLACK POWDER IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 3.1 | 2080 | 1340 | 64 |
| 2 | 3.1 | 2090 | 1255 | 60 |
| 3 | 3.0 | 2060 | 1305 | 63 |
| 4 | 2.8 | 2045 | 1255 | 61 |
| 5 | 3.2 | 1955 | 1200 | 61 |
| AVE | 3.0 | 2046 | 1271 | 61.8 |
| STD DEV | .15 | 53.7 | 53.5 | 1.6 |

TABLE II

FUNCTIONAL DATA ON THE M42C2 PERCUSSION PRIMER USING 200 MG FFG BLACK POWDER IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 5.2 | 1795 | 155 | 8.6 |
| 2 | 5.5 | 1785 | 90 | 5.0 |
| 3 | 4.3 | 1800 | 360 | 20.0 |
| 4 | 5.0 | 1775 | 125 | 7.0 |
| 5 | 5.6 | 1800 | 55 | 3.0 |
| AVE | 5.1 | 1791 | 157 | 8.7 |
| STD DEV | .51 | 10.8 | 119.5 | 2.7 |

TABLE III

FUNCTIONAL DATA ON THE M42C1 PERCUSSION PRIMER USING 200 MG A-CANNON BLACK POWDER IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 8.9 | 1465 | 800 | 54.6 |
| 2 | 9.1 | 1695 | 730 | 43.1 |
| 3 | 15.1 | 1225 | 490 | 40.0 |
| 4 | 7.7 | 1465 | 570 | 38.9 |
| 5 | 12.0 | 1395 | 630 | 45.2 |
| AVE | 10.6 | 1449 | 644 | 44.4 |
| STD DEV | 2.9 | 168.9 | 123.6 | 6.2 |

TABLE IV

FUNCTIONAL DATA ON THE M42C2 PERCUSSION PRIMER USING 200 MG A-CANNON BLACK POWDER IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 13.8 | 1380 | 180 | 13.0 |
| 2 | 16.7 | 1410 | 260 | 18.4 |
| 3 | 15.8 | 1195 | 120 | 10.0 |
| 4 | 19.1 | 1320 | 110 | 8.3 |
| 5 | 16.8 | 1250 | 180 | 14.4 |
| AVE | 16.4 | 1311 | 170 | 12.8 |
| STD DEV | 1.9 | 89.1 | 60 | 3.9 |

TABLE V

FUNCTIONAL DATA ON THE M42C1 PERCUSSION PRIMER USING 200 MG OF TYPE I BORON-POTASSIUM NITRATE IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 32.2 | 845 | 345 | 45.8 |
| 2 | 32.5 | 786 | 156 | 19.8 |
| 3 | 28.3 | 880 | 104 | 11.8 |
| 4 | 23.5 | 904 | 144 | 15.9 |
| 5 | 32.9 | 804 | 100 | 12.4 |
| AVE | 29.8 | 843 | 169 | 20.1 |
| STD DEV | 4 | 49.6 | 100.9 | 11.9 |

TABLE VI

FUNCTIONAL DATA ON THE M42C2 PERCUSSION PRIMER USING 200 MG OF TYPE I BORON-POTASSIUM NITRATE IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 1 | 33.4 | 785 | 25 | 3.1 |
| 2 | 42.2 | 756 | 16 | 2.1 |
| 3 | 37.3 | 742 | 66 | 8.8 |
| 4 | 31.4 | 744 | 56 | 7.5 |

TABLE VI-continued

FUNCTIONAL DATA ON THE M42C2 PERCUSSION PRIMER USING 200 MG OF TYPE I BORON-POTASSIUM NITRATE IGNITION MATERIAL

| TEST NUMBER | TIME TO PEAK PRESSURE (ms) | PEAK PRESSURE (psi) | PRESSURE @ 1ms (psi) | P @ 1ms P PEAK (%) |
|---|---|---|---|---|
| 5 | 39.2 | 748 | 74 | 9.8 |
| AVE | 36.7 | 755 | 47.4 | 6.6 |
| STD DEV | 4.3 | 17.6 | 25.5 | 3.4 |

Finally, and most importantly, ratioing the ignitability of the two primers for each ignition material, the FFG black powder indicated the most differentiation in performance. The FFG black powder ignitability for primer I was 61.8 (Table I) and for primer II, 8.7 (Table II) producing a ratio of 7.1. For the A-cannon black powder, the ratio was 3.5, and for the Type I $BKNO_3$, the ratio was 3.0.

Although ignition is a major requirement for systems such as aerospace rocket motors, munitions and even automobile air bags, no method currently exists, other than the present invention, to measure relative ignition efficiency, or "ignitability." Consequently, no specification exists on ignitability, and surprisingly, there are no output test requirements in any military specification for percussion primers which are used only for initiation.

The key parameters for achieving a successful test methodology and bomb configuration and acceptable pressure performance differentiation between primers were determining the proper ignition material and its confinement. The fine ignition materials, which were easily initiated and exhibited very high burn rates, produced similar pressure traces with either primer. Conversely, the large pellet ignition materials initiated and burned so slowly that the pressure traces were again similar with either primer. The ignition material had to be confined in a holder at the top of the test bomb cavity, facing the percussion primer, rather than in the bottom of the cavity to achieve reproducible pressure performances. This confinement provided highly reproducible initial conditions and allowed primer output to penetrate and mix with the igniter material to achieve ignition. Furthermore, the small initial volume sustained the initial primer output pressure, supporting the conditions needed for stable combustion. This configuration has the added benefit of providing a good simulation of actual design interfaces.

The present method clearly differentiates the ignition performances of two different percussion primers. The pressure traces produced by each primer, test-fired with FFG black powder, A-cannon black powder and Type I boron-potassium nitrate ($BKNO_3$), were markedly different in any combination. Recorded for statistical comparisons were the times to peak and 50 percent of peak pressure, the peak pressure, and a term defined herein as "ignitability." Ignitability is defined as the ratio of the pressure achieved within the first millisecond over the peak pressure. The first millisecond is when the major portion of primer output is produced to initiate the ignition materials.

The FFG black powder proved to be the best ignition material in the test, followed by A-cannon black powder and Type I $BKNO_3$, to evaluate the differences in output performance of the two percussion primers. The most dramatic single data point comparator was ignitability. The ignitability of primer I, using the FFG black powder, was 7.1 times greater than that produced by the primer II.

Primer output delays for the M42C1 and M42C2 are shown in Table VII along with further data on time to peak pressure, function time, peak pressure, pressure of 1ms and ignitability factor.

TABLE VII

PERFORMANCE AT +75° F. USING 200 MG FFG BLACK POWDER

| MAX. AVG. MIN. (STD. DEV.) | M42C1 | M42C2 |
|---|---|---|
| Primer output delay, ms | .368 | 10.55 |
|  | .333 | 3.60 |
|  | .260 | .68 |
|  | (.039) | (2.74) |
| Time to peak pressure, ms | 3.8 | 6.4 |
|  | 3.4 | 4.5 |
|  | 2.9 | 3.7 |
|  | (.3) | (.63) |
| Function time, ms | 4.0 | 14.7 |
|  | 3.7 | 8.7 |
|  | 3.2 | 5.7 |
|  | (.35) | (5.2) |
| Peak pressure, psi | 2160 | 2060 |
|  | 2073 | 1917 |
|  | 2020 | 1690 |
|  | (53) | (138) |
| Pressure at one ms, psi | 1540 | 570 |
|  | 1405 | 478 |
|  | 1260 | 400 |
|  | (110) | (61) |
| Ignitability factor, % | 74.8 | 45.9 |
|  | 67.8 | 27.7 |
|  | 59.3 | 19.6 |
|  | (5.4) | (7.8) |

The many features and advantages of the present invention are apparent from the detailed specification, and thus, it is intended by the appended claims to cover all such features and advantages of the ignitability test method and apparatus which fall within the true spirit and scope of the invention. Further, since numerous modifications and changes will readily occur to those skilled in the art based upon the disclosure herein, it is not desired to limit the invention to the exact construction and operation illustrated and described. Accordingly, all suitable modifications and equivalents may be resorted to falling within the scope and the spirit of the invention.

What is claimed is:

1. An apparatus for testing ignitability of an initiator, comprising:
    a body having a central cavity, an upper cavity and a lower cavity, the upper and lower cavities being disposed at opposite ends of the central cavity and collectively forming with the central cavity a central passageway passing through the body;
    an initiator holder for holding the initiator over the central cavity of the body;
    an ignition material holder disposed in the central cavity of the body and having a cavity facing the initiator holder which receives a measured quantity of ignition material to be ignited by the initiator and a chamber in communication with the cavity of the ignition material holder and the central cavity of the body;
    an adaptor removably mounted in the upper cavity and abutting the upper end of the initiator holder;
    a firing mechanism slidably received in a bore extending through the adaptor and being movable into contact with the initiator, thereby firing the initiator;

a drop weight means to provide actuation of the firing mechanism;

a guiding means to guide the drop weight means to concentrically impact of the firing mechanism;

an accelerator means mounted above the drop weight means to record time of impact of the firing mechanism by the drop weight means; and means, in communication with the central cavity of the body, for measuring pressure characteristics generated by ignition of the ignition material by the initiator.

2. An apparatus for testing ignitability as claimed in claim 1, wherein the measuring means comprises at least one transducer mountable in the body to be in communication with the central cavity and outputting a signal indicative of pressure generated upon firing of the initiator into the ignition material, and an instrument for measuring and recording the pressure as a function of time.

3. An apparatus for testing ignitability as claimed in claim 2, wherein the analyzing means further comprises means for determining pressure at one millisecond after firing the initiator and peak pressure, the ratio of one millisecond pressure to peak pressure defining a value of ignitability.

4. An apparatus for testing ignitability as claimed in claim 2, wherein the at least one transducer is a piezoelectric transducer.

5. An apparatus for testing ignitability as claimed in claim 2, wherein the analyzing means comprises a magnetic tape recorder and oscillograph coupled to and recording the output of a transducer which is mountable in the body to sense ignition-induced pressure.

6. An apparatus for testing ignitability as claimed in claim 2, wherein the at least one transducer is mounted orthogonally to a longitudinal axis of the ignition material holder at a position spaced above the radially oriented holes of the ignition material chamber.

7. An apparatus for testing ignitability as claimed in claim 1, wherein the ignition material cavity is hemispherically shaped.

8. An apparatus for testing ignitability as claimed in claim 2, wherein the analyzing means further comprises means for determining output delay by recording the time interval between impact of the firing mechanism as indicated by the accelerometer means and pressure in the central cavity reaching 100 psi.

9. A method for testing ignitability of an initiator comprising determining an output delay and a function time of an initiator and determining a ratio of a one millisecond pressure value to the peak pressure, the ratio of said pressure values defining a value of ignitability, and comparing the ratio to ratios corresponding to other combinations of initators and ignition materials similarly tested to determine relative differences in ignitability.

* * * * *